(12) United States Patent
Bynum

(10) Patent No.: US 6,202,708 B1
(45) Date of Patent: Mar. 20, 2001

(54) FILLABLE CASSETTE APPARATUS AND METHOD

(75) Inventor: Gail Bynum, Brooklyn Park, MN (US)

(73) Assignee: SIMS Deltec, Inc., St. Paul, MN (US)

( * ) Notice: Subject to any disclaimer, the term of this patent is extended or adjusted under 35 U.S.C. 154(b) by 0 days.

(21) Appl. No.: 09/189,379

(22) Filed: Nov. 9, 1998

(51) Int. Cl.[7] .................................. B65B 1/04; B65B 3/04
(52) U.S. Cl. ........................ 141/9; 141/105; 141/106; 141/107; 141/114; 141/311 R; 141/313; 141/319; 141/329; 604/518; 604/520; 604/86
(58) Field of Search .................. 141/2, 9, 18, 100, 141/105–107, 113, 114, 311 R, 313, 319, 329, 330; 604/500, 518, 520, 82–92; 128/DIG. 12, DIG. 13

(56) References Cited

U.S. PATENT DOCUMENTS

| | | | |
|---|---|---|---|
| 4,391,598 | * | 7/1983 | Thompson .............................. 604/65 |
| 4,398,908 | | 8/1983 | Siposs . |
| 4,410,321 | | 10/1983 | Pearson et al. . |
| 4,458,733 | * | 7/1984 | Lyons ................................... 141/1 |
| 4,559,038 | | 12/1985 | Berg et al. . |
| 4,657,486 | | 4/1987 | Stempfle et al. . |
| 4,792,329 | | 12/1988 | Schreuder . |
| 4,871,351 | | 10/1989 | Feingold . |
| 5,116,316 | * | 5/1992 | Sertic et al. ............................ 604/83 |
| 5,176,634 | | 1/1993 | Smith et al. . |
| 5,353,961 | | 10/1994 | Debush . |
| 5,462,526 | | 10/1995 | Barney et al. . |
| 5,478,211 | | 12/1995 | Dominiak et al. . |
| 5,480,386 | | 1/1996 | Brohy et al. . |
| 5,531,697 | | 7/1996 | Olsen et al. . |
| 5,538,399 | | 7/1996 | Johnson . |
| 5,547,470 | * | 8/1996 | Johnson et al. ......................... 604/67 |
| 5,558,639 | | 9/1996 | Gangemi et al. . |
| 5,577,369 | | 11/1996 | Becker et al. . |
| 5,695,473 | | 12/1997 | Olsen . |

OTHER PUBLICATIONS

Brochure, "The ADD–Vantage System: Adding up the Benefits for Your Pharmacy", Abbott Laboratories, North Chicago, Illinois (May 1996).

* cited by examiner

Primary Examiner—Timothy L. Maust
(74) Attorney, Agent, or Firm—Merchant & Gould P.C.

(57) ABSTRACT

A cassette is described including a housing, an inner reservoir located within the housing, a valve coupled to the inner reservoir and coupled to the housing, and a delivery conduit coupled to the inner reservoir and emerging from the delivery opening of the cassette. The cassette also includes a dispensing apparatus that defines a passage and has a first activating device that opens the valve of the cassette. The dispensing apparatus also has a second activating member capable of establishing fluid communication with a medicant container. A method of mixing a powdered drug and a liquid includes establishing fluid communication between the reservoir and the medicant container, dispensing at least a portion of the liquid into the medicant container, and transferring the mixed drug into the reservoir. A method of filling a cassette includes the steps of introducing the drug into the cassette, closing a first access port, evacuating the inner reservoir through a second access port, and introducing the drug to fill the cassette through the first access port.

14 Claims, 12 Drawing Sheets

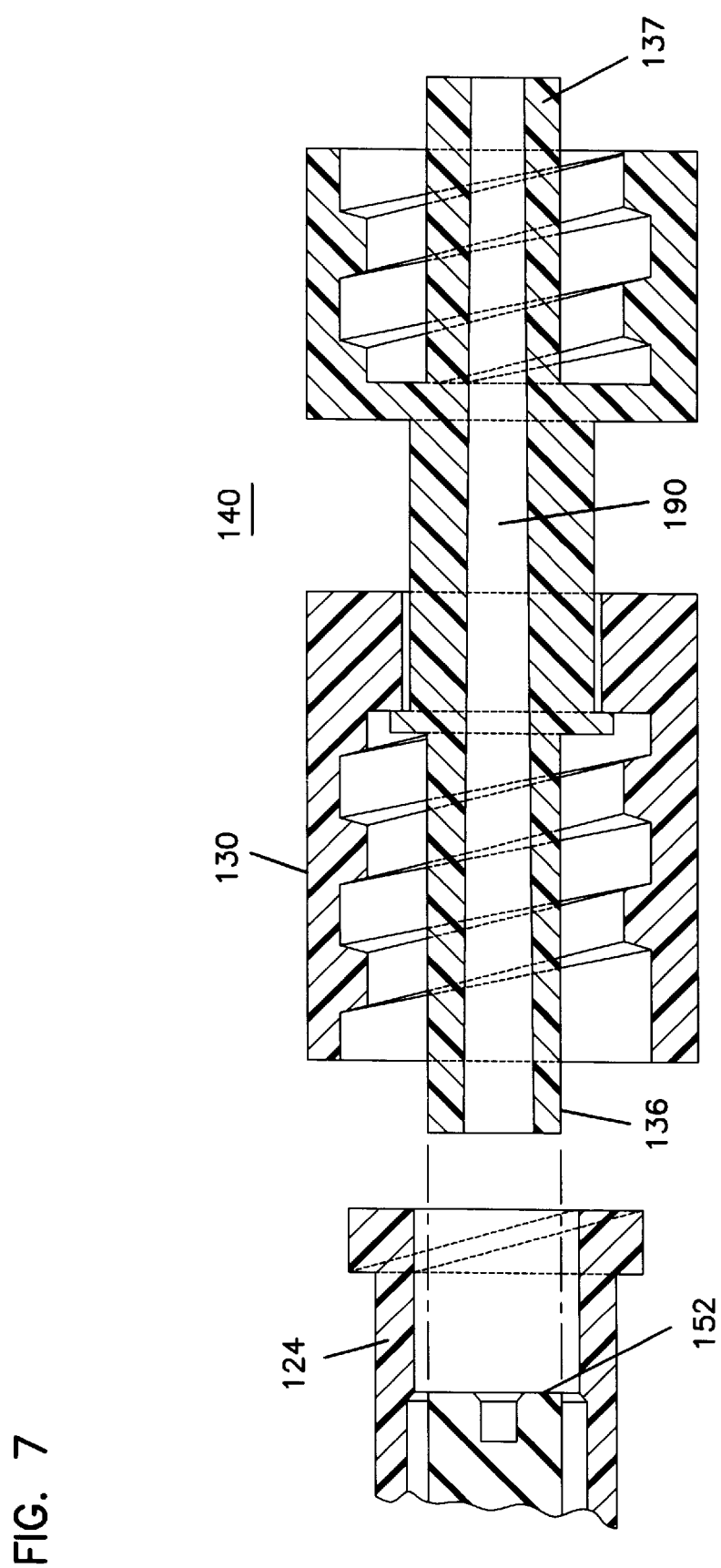

FILLABLE CASSETTE APPARATUS AND METHOD

FIELD OF THE INVENTION

The present invention is directed to a cassette for use with a drug pump for administering drugs and a method for administering drugs, and more particularly to a cassette and method that allows improved filling of a cassette with a drug.

BACKGROUND OF THE INVENTION

Various ambulatory medical devices are known for treating and/or monitoring patients at a remote site away from the caregiver's or clinician's office. One example of an ambulatory medical device is a drug delivery device, such as a drug pump, for providing periodic or continuous drug delivery to the patient when the patient is away from the caregiver's office. Ambulatory drug pumps are shown for example in U.S. Pat. Nos. 4,559,038, 5,531,697 and 5,695,473, the disclosures of which are incorporated by reference.

Certain drugs rarely achieve their maximum therapeutic action through conventional injection techniques. Many drugs reach their full potential only through precise delivery over an extended period of time. With controlled drug infusion through a drug pump, the drug can be given at a precise rate that will keep the drug concentration within the therapeutic margin and out of the toxic range. Ambulatory drug pumps can provide appropriate drug delivery to the patient at a controllable rate which does not require frequent medical attention and which allows the patient to leave the hospital or caregiver's office.

Ambulatory drug pumps typically provide the patient with a drug or agent in liquid form, administering the liquid to the patient through a flexible conduit. Some drugs are sold in a powdered form. Examples of drugs on the market today that are sold in powder form include ampicillin, vancomycin hydrochloride, penicillin, nafcillin, and Desferal™ deferoxamine mesylate. Before powdered drugs are administered, they must be mixed with a liquid agent. When powdered drugs are dispensed at pharmacies, the pharmacist typically adds a liquid agent, such as a diluent, to the powdered drug at the pharmacy and then gives the drug to the patient in a liquid form, for example, in a drug pump cassette. The patient could then use the liquid drug with an ambulatory drug pump. Examples of liquid agents that may be mixed with powdered drugs are sterile water, dextrose and saline. These mixing steps require significant pharmacist time and may cause a long wait for a patient who is filling the prescription. Current ambulatory drug pump cassettes do not conveniently allow the patient to perform the dilution or reconstitution of a powdered drug, so the patient must visit the pharmacist.

Certain types of drugs, such as ampicillin, have limited stability in liquid form. These drugs must be mixed with a liquid agent only a short period of time before they are administered to the patient. The short-lived stability of these drugs necessitates frequent trips by the patient to pick up the diluted drug or frequent deliveries of the diluted drug to the patient's location. In the alternative, some patients are taught to mix drugs with a liquid agent at home. If known drug cassette configurations are used, this process may be awkward and cumbersome for the patient.

Another problem with filling cassettes for ambulatory drug pumps is the elimination of air from the reservoir within the cassette. Typically, cassettes are filled by injecting fluid through a delivery conduit that is connected to the cassette reservoir. The delivery conduit is a tube that connects the cassette to the patient for drug delivery. Pharmacists will typically use a syringe or a pump to move the drug to be administered into the cassette reservoir. After the cassettes are filled, however, trapped air may be present in the cassette reservoir. Typically, the pharmacist will manually remove the trapped air from the cassette reservoir.

In one technique for manually removing trapped air, the cassette is tapped until all the air bubbles have collected, and can be drawn out with a syringe. This process is repeated until all of the air bubbles have been removed. The method is time-consuming and labor-intensive for the pharmacist.

There is a need for drug delivery systems and methods which address the above-mentioned concerns, concerns about drugs that require dilution and/or reconstitution before administration, and concerns about trapped air in the cassette reservoir.

SUMMARY OF THE INVENTION

The present invention concerns a drug pump cassette, including a housing that defines a transfer opening and a delivery opening. The cassette also includes an inner reservoir located within the housing. An access device, or valve, is also provided on the cassette. The valve has a first portion coupled to the inner reservoir at a transfer port and has a second portion coupled to the housing at the transfer opening. The cassette also includes a delivery conduit coupled to the inner reservoir at a delivery port, and emerging from the delivery opening of the cassette.

Preferably, the housing further includes a pressure plate supporting a portion of the delivery conduit. The pressure plate may be mounted to a control module of a pump.

The drug cassette may also include a dispensing apparatus. The dispensing apparatus defines a passage and has a first activating device and a second activating device. The first activating device of the dispensing apparatus opens the valve of the cassette. The second activating device establishes fluid communication with a medicant container. The second activating device may include a spike used to pierce a septum of the medicant container, and an air vent to the atmosphere. The air vent may be provided with a filter.

In one method in accordance with the present invention, a liquid from a cassette is mixed with a powdered drug in a medicant container and the mixture is transferred back to the cassette. In an alternative method, a liquid from a container is mixed with a powdered drug in a cassette reservoir.

In a method for filling a cassette in accordance with the present invention, the inner reservoir of the cassette is evacuated through a second access port before filling the inner reservoir with the drug through the first access port, thereby providing a filled cassette with minimized trapped air.

BRIEF DESCRIPTION OF THE DRAWINGS

FIG. 7 is a cross-sectional side view of a first portion of a second embodiment of a dispensing apparatus of the present invention.

DESCRIPTION OF THE PREFERRED EMBODIMENTS

The present invention is applicable to a variety of systems and arrangements which are used to mix drugs before administration or to fill a cassette while minimizing trapped air before administration. The invention is advantageous in environments where a drug requires dilution or reconstitution immediately before administration. A cassette is described herein that allows a person, such as a patient, to easily mix a powdered drug with a liquid for administration with an ambulatory drug pump. The cassette of the present invention further enables the filling of the cassette so that trapped air is minimized.

The cassette of the present invention includes an access mechanism that allows a user to empty at least a portion of liquid contents of the cassette into a medicant container to mix and/or dilute the drug in the container. The access mechanism then allows the user to transfer the mixed together contents of the container to the cassette for use with the drug pump. Alternatively, the access mechanism allows a user to add liquid to a powdered drug in the cassette. The access mechanism further permits evacuation of an inner reservoir of the cassette so that trapped air in the inner reservoir and a delivery conduit can be reduced before filling with a liquid drug.

Figure 9:
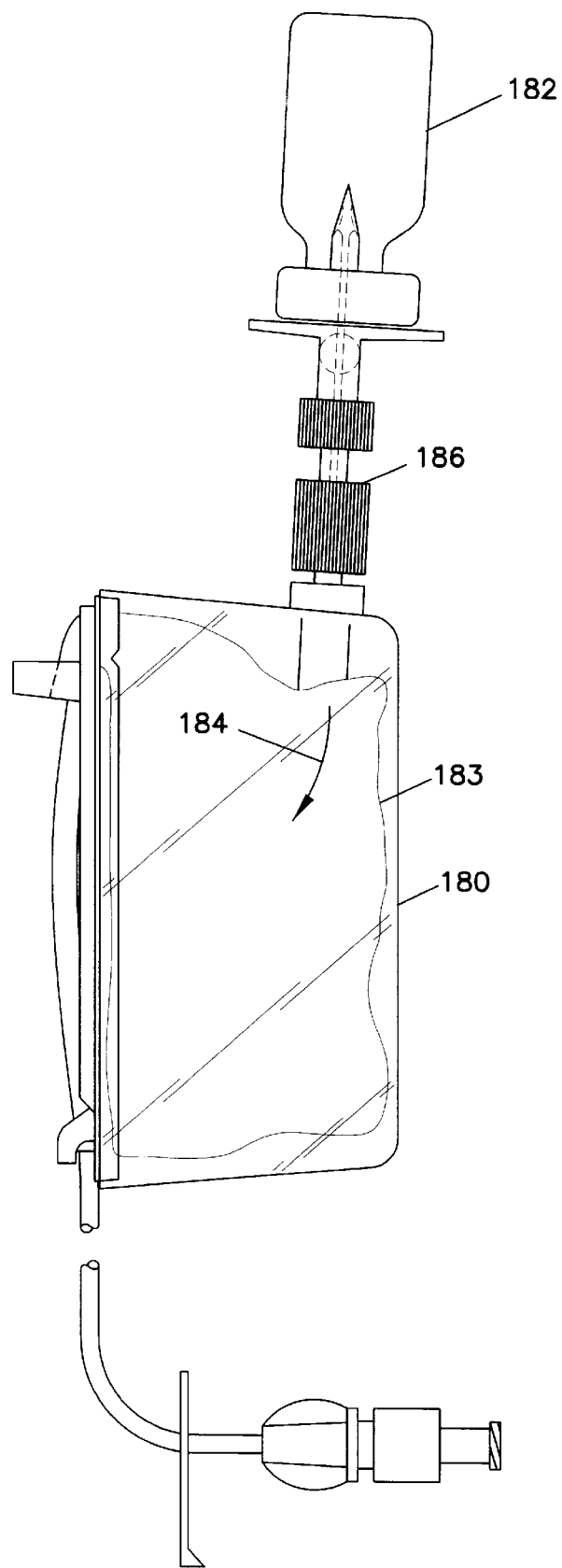
FIG. 9 is a side view of an alternative embodiment of the cassette of the present invention where the components are connected in which an inner reservoir contains a powdered drug and a medicant container contains diluent liquid.
Figure 10:
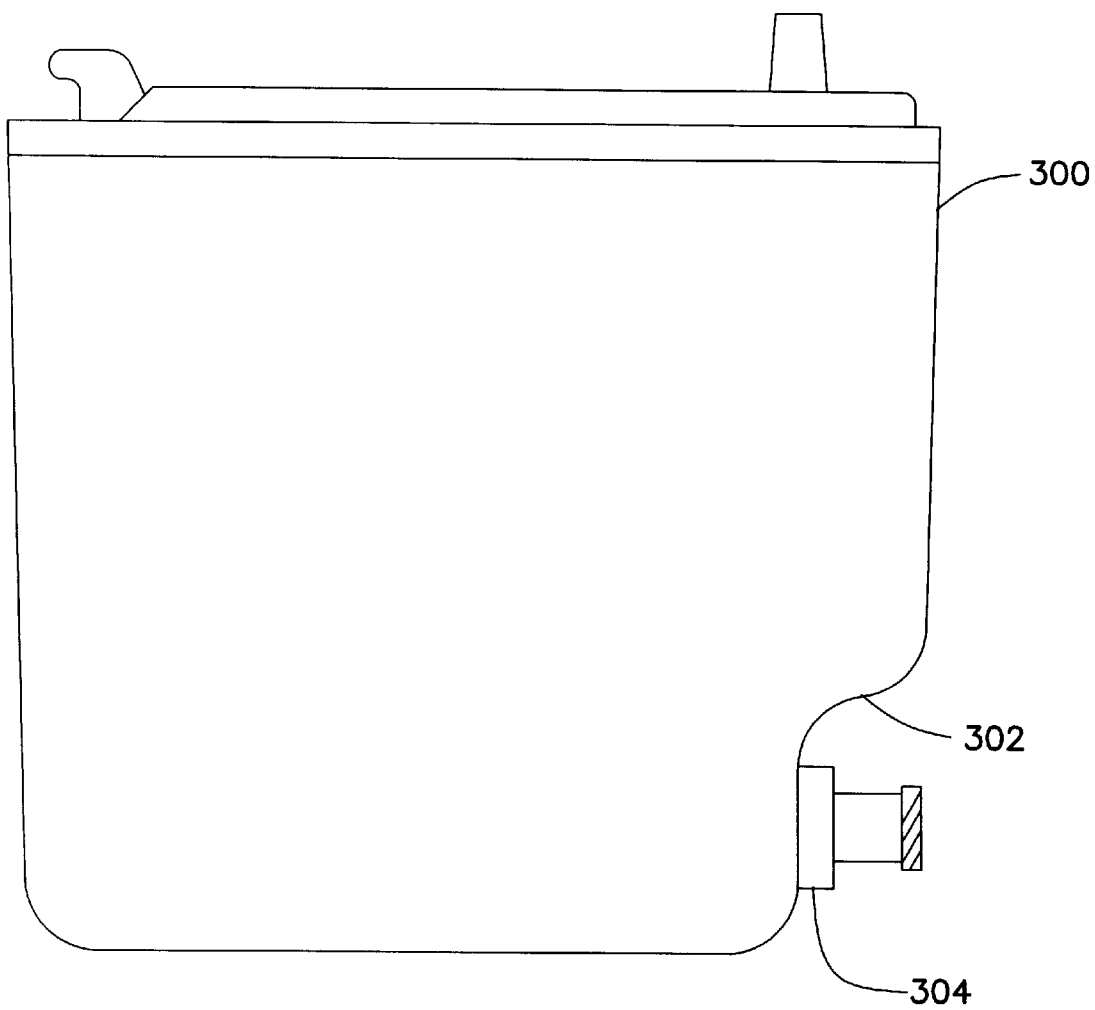
FIG. 10 is a side view of an alternative embodiment of a cassette for use when mixing a drug or when using a method of the present invention to fill the cassette while minimizing trapped air.
Figure 11:
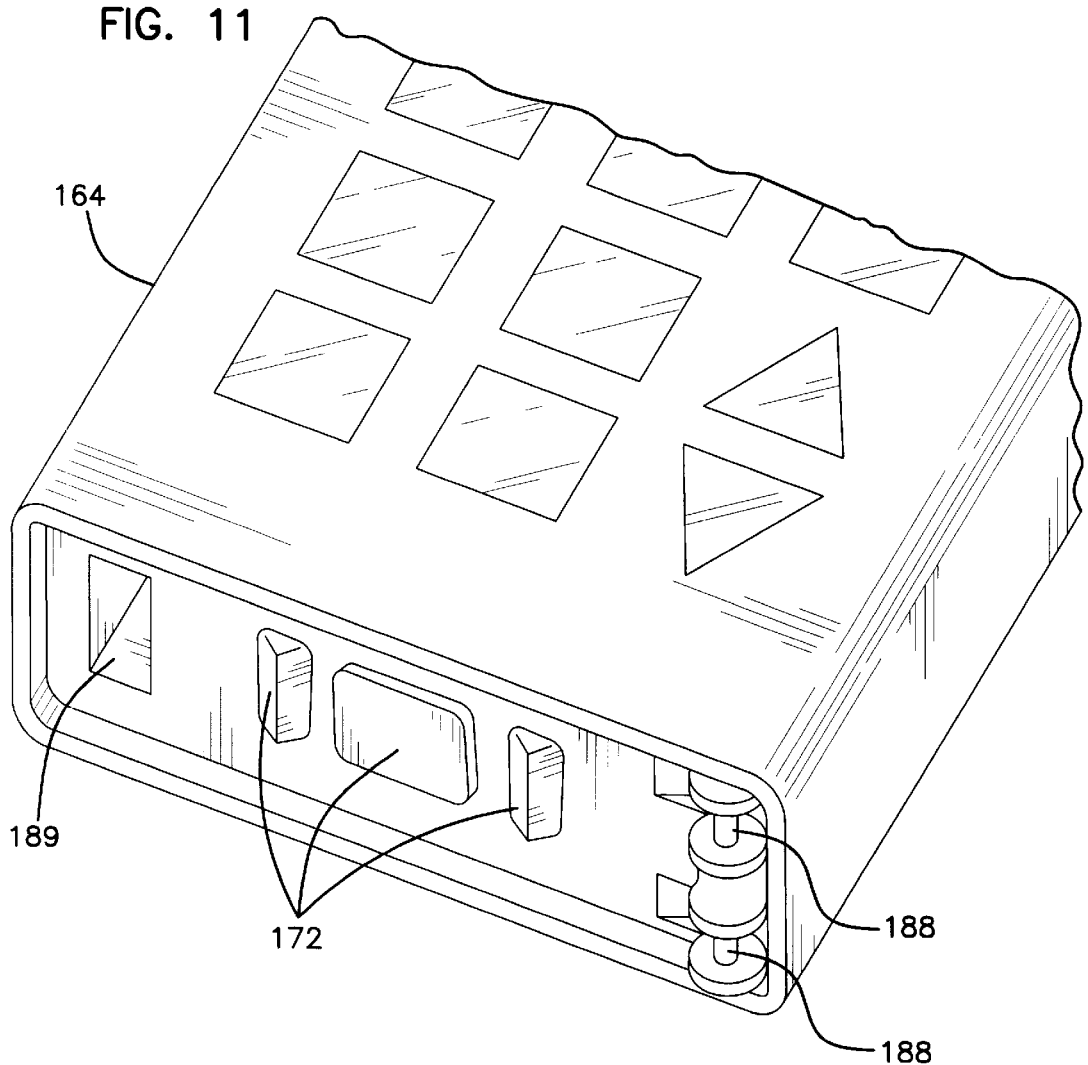
FIG. 11 is a perspective view of a drug pump control module.

Referring now to FIGS. 1–12, a system 20 including a cassette 100, a dispensing apparatus 102, and a medicant container 104 is shown according to one embodiment of the present invention. The cassette 100 is designed for use with a drug pump (or control module) 164 as shown in FIG. 11. A pressure plate 106 of the cassette 100 mounts to the control module 164 with two hooks 166 and an anchor 168, illustrated in FIG. 1. The two hooks 166 engage two pins 188. A latch 189 within the control module engages the anchor 168. The cassette 100 further includes an inner reservoir 108, such as a flexible polymeric bag. During administration of a liquid drug to a patient, the inner fluid reservoir 108 will contain the liquid drug. The inner fluid reservoir includes two openings: a delivery port 110 and a transfer port 112, illustrated in FIG. 2.

The two ports 110, 112 of the inner reservoir 108 each communicate with openings in a housing 114 of the cassette 100. The housing 114 defines a delivery opening 116 and a transfer opening 118. At the delivery port 110 of the inner reservoir 108, the inner reservoir 108 is connected to a delivery conduit 120, such as a compressible polymeric tube that emerges from the delivery opening 116 of the housing 114. The delivery conduit 120 is supported by the pressure plate 106 of the cassette 100. The portion of the delivery conduit that is supported on the pressure plate 106 is the pump portion 122 of the delivery conduit 120. In the illustrated embodiment, the pump portion 122 may be larger in size than the remainder of the delivery conduit 120. When the cassette 100 is mounted to the control module 164, a pumping mechanism 172 (FIG. 11) of the control module 164 will act on the pump portion 122 to draw the liquid drug out of the inner reservoir 108 and move it along the delivery conduit 120. The delivery conduit 120 is connected to a patient for drug delivery. A luer fitting 109 or another type of connector and a cap 111 may be provided at the end of the delivery conduit 120.

Figure 5A:
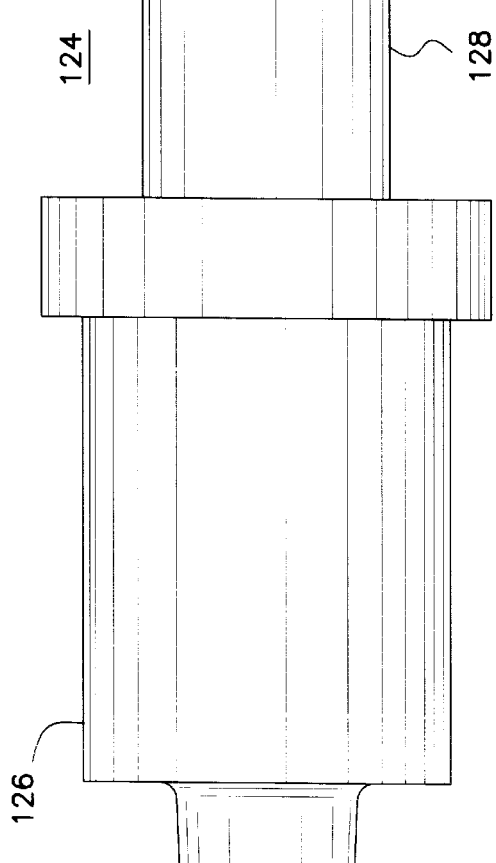
FIG. 5A is a side view of a luer-activated valve that may be used with the cassette of FIG. 1.
Figure 5B:
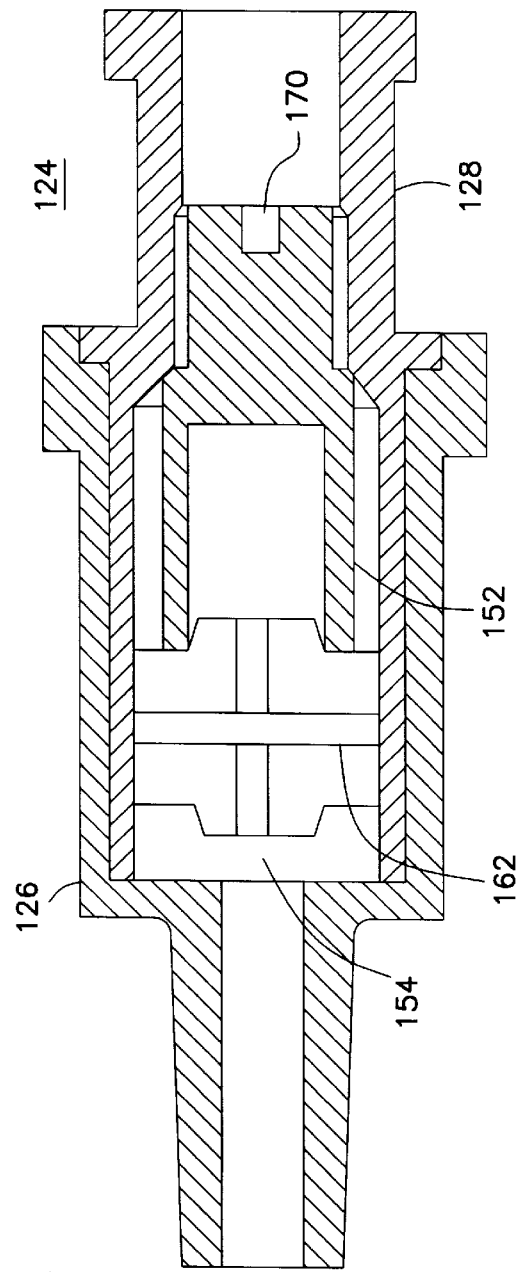
FIG. 5B is a cross-sectional side view of the luer-activated valve of FIG. 5A.

The cassette 100 also includes an access mechanism for allowing selective access to the interior of the inner reservoir 108. One preferred access mechanism includes a valve 124 capable of establishing fluid communication with the inner reservoir 108 in order to allow mixing with the contents of another container, such as the medicant container 104. A dispensing apparatus 102 links the valve 124 of the cassette 100 with the medicant container 104. The valve 124 of the illustrated preferred embodiment includes a first portion 126 that is operatively coupled to the inner fluid reservoir 108 at port 112. The valve 124 further includes a second portion 128 that is attached to the housing 114 of the cassette 100 at transfer opening 118. The valve 124 is capable of establishing fluid communication with the dispensing apparatus 102 when activated by the dispensing apparatus 102. The valve 124 may be, for example, a luer-activated valve having a stopping member 152 that can be depressed by a luer fitting to open a passage 154, as illustrated in FIGS. 5A and 5B. A biasing member 162 holds the stopping member 152 into engagement with the interior neck portion of the valve 124. For use with such a luer-activated valve, the first activating member 130 of the dispensing apparatus 102 may be a luer fitting that depresses the stopping member 152. Many luer-activated valves are commercially available that may vary from the valve shown in FIGS. 5A and 5B, but could be used with the present invention.

Dilution of a drug, where the concentration of an active material is reduced, may easily be practiced using the present invention. The present invention is useful where two drug components must be mixed prior to administration to a patient using a cassette. Possible drug mixtures that could be carried out with the present invention include combining two liquids, or a solid and a liquid.

In use, the cassette 100 is attached to the dispensing member 102, and fluid communication is established between the dispensing member 102 and the medicant container 104. In a preferred embodiment, the cassette 100 will initially contain a liquid diluent 107 to be mixed with a powdered drug. Examples of diluents include sterile water, saline, and dextrose. The cassette 100 may also initially contain another type of liquid agent for mixing with a powdered drug.

Figure 1:
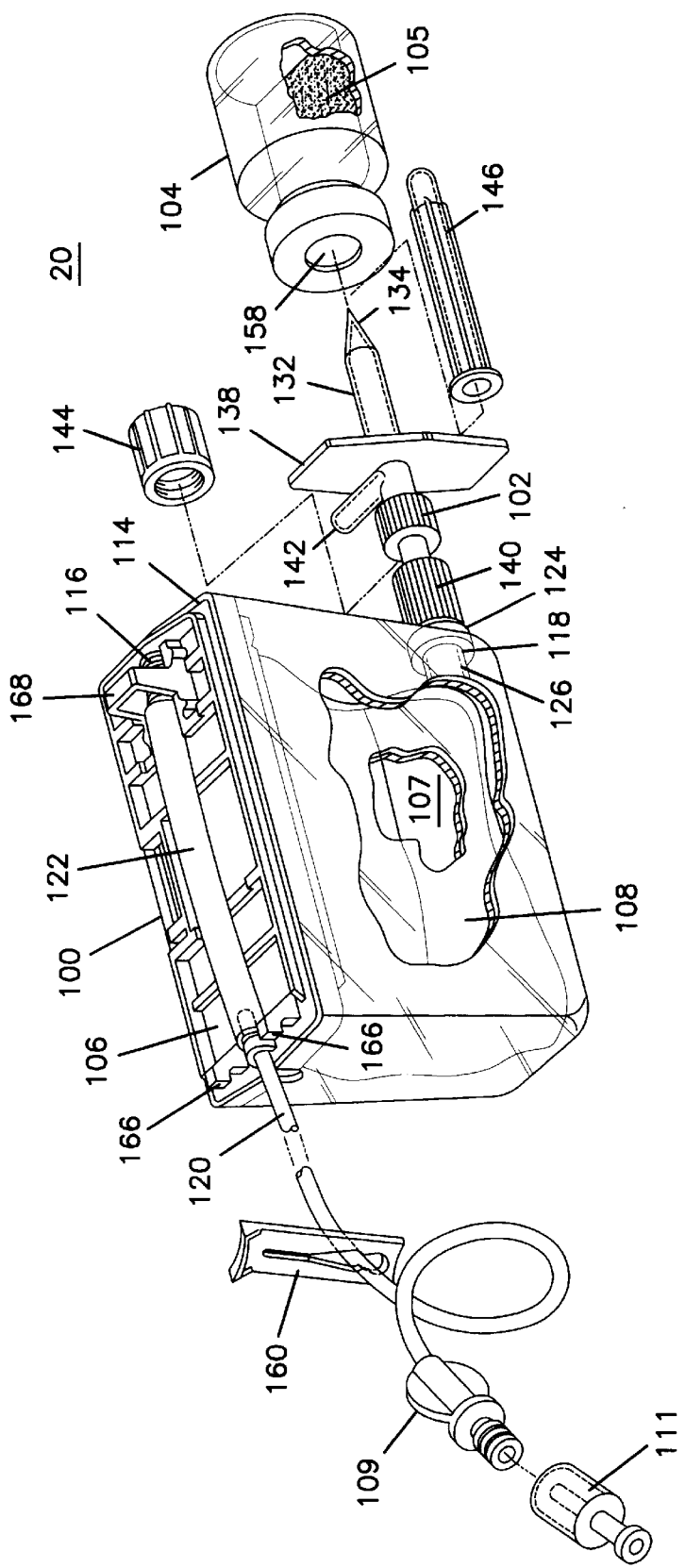
FIG. 1 is a perspective view of one embodiment of a cassette for use with a drug, a dispensing apparatus, and a medicant container.
Figure 2:
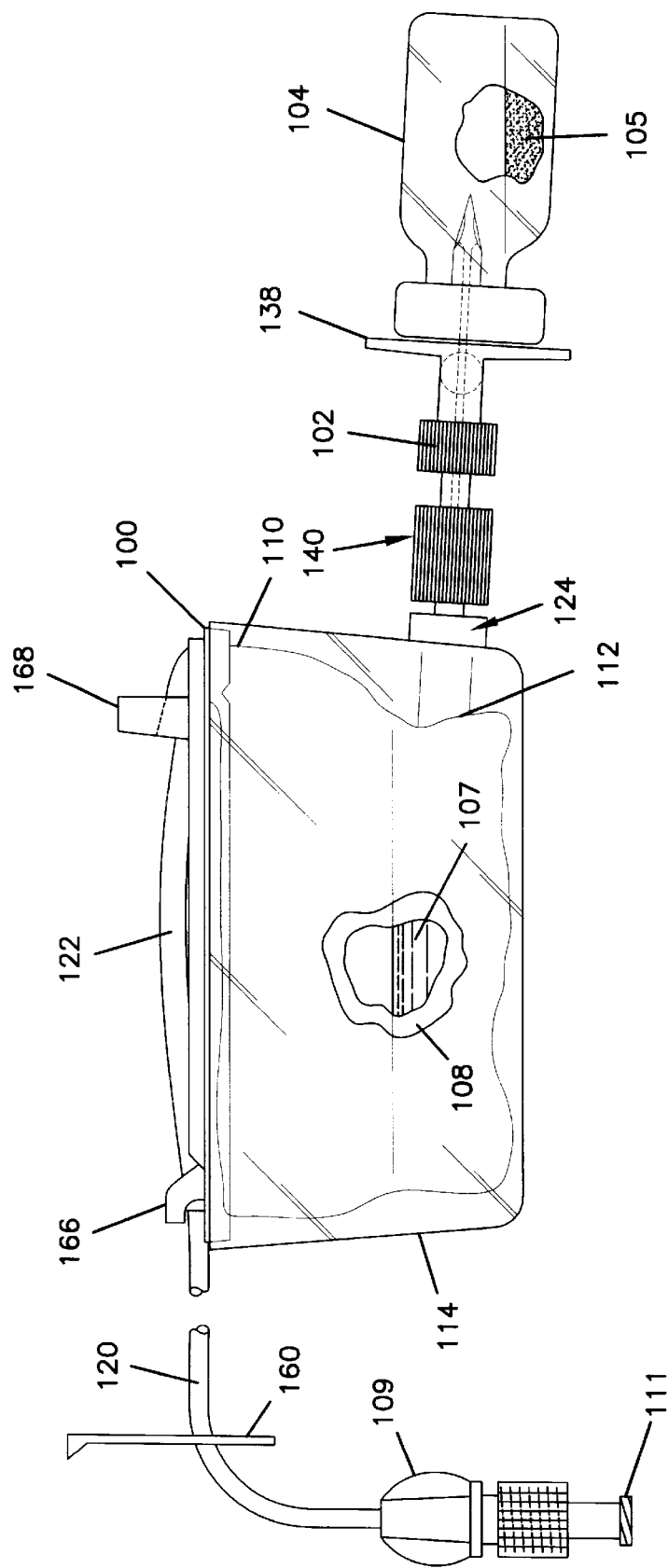
FIG. 2 is a side view of the cassette of FIG. 1 where the components are connected.

In the embodiment of FIG. 1, the medicant container 104 initially contains a powdered drug 105 to be administered to a patient. The dispensing apparatus 102 has a second activating member 132 for establishing fluid communication with the medicant container 104. The medicant container 104 may be a vial with a sealed, pierceable septum 158. In this case, the second activating member is a spike 134 that pierces the septum 158 and provides a passageway to the valve 124. As discussed above, the dispensing apparatus also has a first activating member that is designed to open the valve 124, such as a luer fitting if valve 124 is a luer-activated valve.

In the embodiment illustrated in FIG. 1, the dispensing apparatus 102 includes two parts, a vented dispensing pin 138 and a male-to-male luer adapter 140. However, a one piece dispersing apparatus 200 could be used in place of the two piece dispensing apparatus 102. The one piece dispensing apparatus is illustrated in FIGS. 6A–6C and is discussed further below.

Figure 8A:
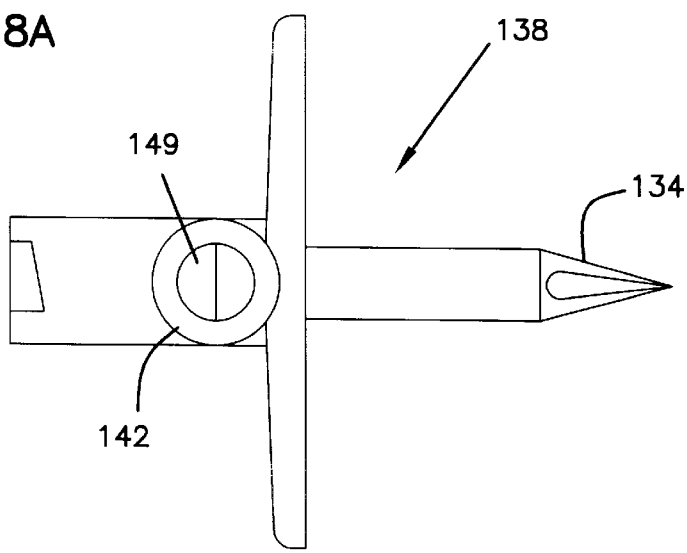
FIG. 8A is a front view of a second portion of the second embodiment of the dispensing apparatus of the present invention.
Figure 8B:
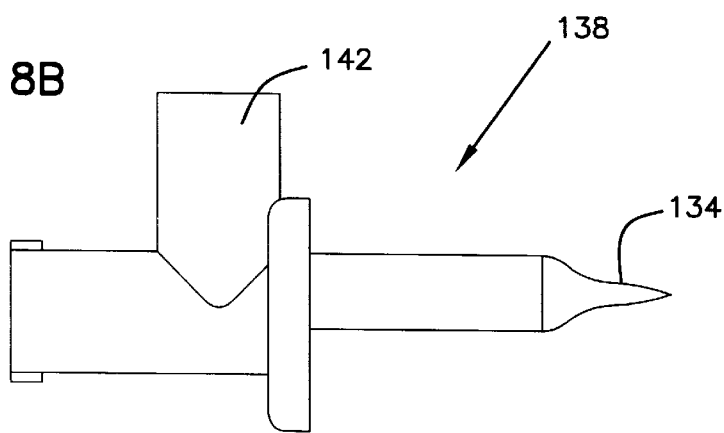
FIG. 8B is a side view of the second portion of the dispensing apparatus of FIG. 8A.
Figure 8C:
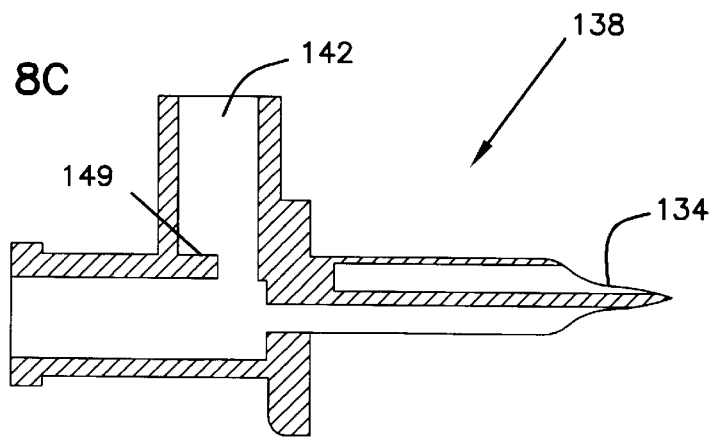
FIG. 8C is a cross-sectional side view of the second portion of the dispensing apparatus of FIG. 8A.

The two piece dispensing apparatus 102 is illustrated in FIG. 1. The venting dispensing pin 138 includes the second activating member, or spike, 134, as shown in FIGS. 8A–8C. The male-to-male luer adapter 140 includes the first activating member, a luer 136 for activating the valve 124 as shown in FIG. 7. The vented dispensing pin 138 includes a luer lock that attaches to the opposite end of the male-to-male luer adapter 140, providing a passage for fluid communication.

The dispensing apparatus 102 may be provided with an air vent 142 to more easily enable the flow of liquid between the cassette and the medicant container 104 by permitting displaced air or other gas to escape and allowing air to enter the connected cassette assembly, specifically the medicant container 104. The air vent 142 is constructed according to known methods for permitting the flow of gas, but preventing the flow of liquid. For example, the air vent 142 may include a hydrophobic membrane that is penetrable by gases but not by fluids. Vented dispensing pin 138 and male-to-male luer adapter 140 are commercially available as separate components. One example of a dispensing pin 138 that could be used as a portion of the dispensing apparatus 102 is the DP-1000 Mini-Spike® dispensing pin assembly, manufactured by Burron OEM, a division of B. Braun Medical, Inc.

Figure 6A:
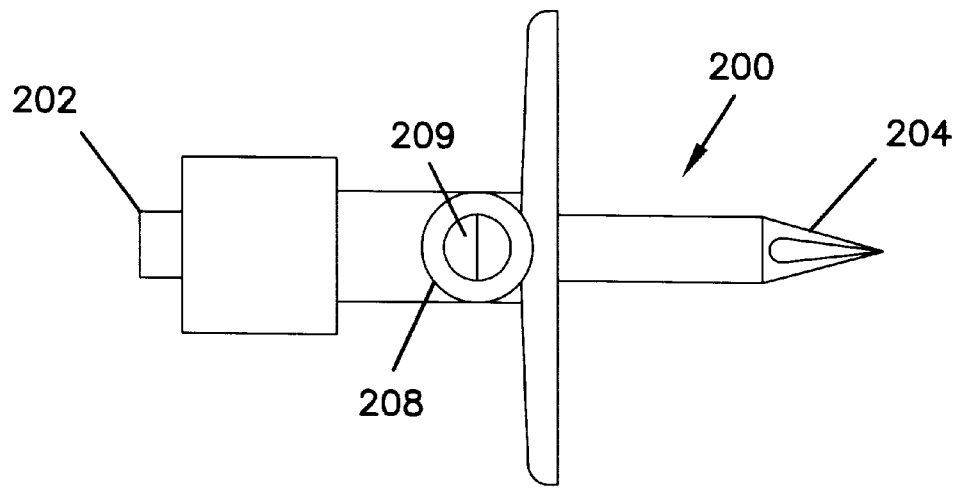
FIG. 6A is a front view of a first embodiment of a dispensing apparatus for use with the present invention.
Figure 6B:
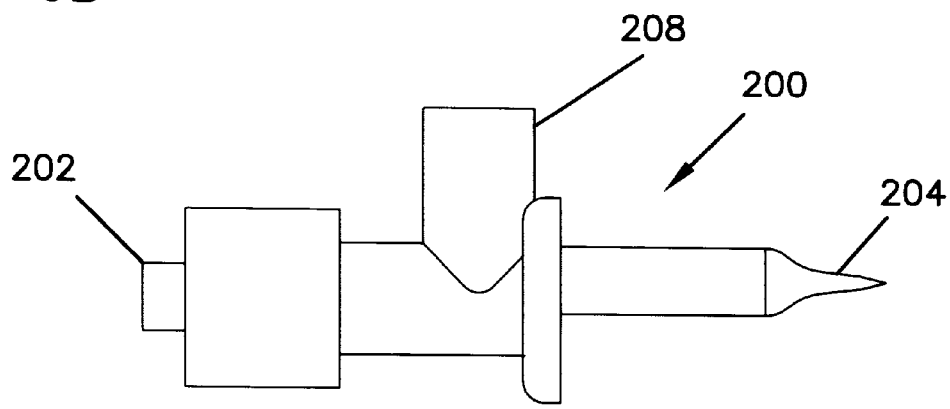
FIG. 6B is a side view of the dispensing apparatus of FIG. 6A.
Figure 6C:
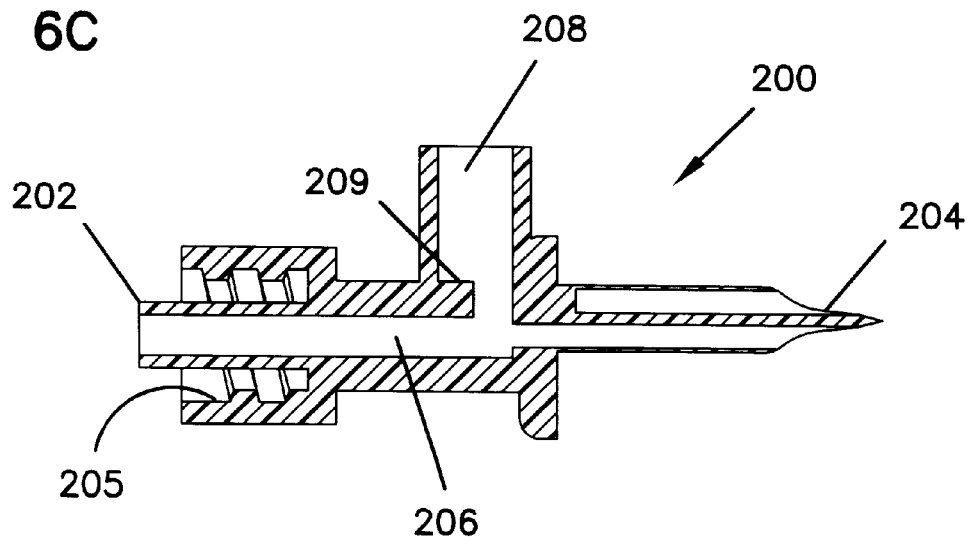
FIG. 6C is a cross-sectional side view of the dispensing apparatus of FIG. 6A.

Referring now to FIG. 6A and FIG. 8A, the preferred air vents 142 and 208 are similarly constructed. In the preferred embodiment, the liquid does not typically flow out of the air vent during filling or mixing, because the fluid tends to flow down the path of least resistance, therefore through the center passageway of dispensing pin. Another factor which prevents the air vent of the present invention from leaking fluid is the capillary action of the small tip of the spike tip. This spike tip and its small passage discourages flow toward the vent opening. In addition, a half-shield structure 149 or 209 at the vent 142 or 208 blocks some fluid flow out of the vent 142 or 208.

One example of a male-to-male luer adapter 140 that could be used as part of the dispensing apparatus 102 is the male/male luer lock connector, Model No. B1000200, manufactured by Burron OEM, a division of B. Braun Medical, Inc. The male-to-male luer adapter may be constructed of polycarbonate ABS, polypropylene or other similar material and is shown in FIG. 7 in detail. The adapter 140 defines a passage 190. The luer fitting 136 of the adapter 140 depresses the stopping member 152 of the valve 124 when the adapter 140 is connected to the valve 124. A second luer fitting 137 may also be included on the adapter 140. A cap 144 may be used to protect the valve 124 before and after the mixing process and maintain aseptic conditions.

In an alternative embodiment, a dispensing apparatus 200 could be made of only one piece as shown in FIGS. 6A–6C, having both a first activating member 202 and a second activating member 204 on the same body connected in a permanent manner. In this embodiment there are fewer components for a user to connect.

The one-piece dispensing apparatus 200 may include a luer fitting as the first activating member 202. The first activating member 202 is designed to establish fluid communication with the valve 124. The first activating member 202, or luer, may also include threads along the wall 205, for receiving and securing the luer-activated valve or other type of valve. The threads would be similar to those illustrated in FIG. 7 near the activating members 136 and 137. A second activating member 204 may be a spike to pierce the septum of the medicant vial. The one-piece dispensing apparatus 200 also defines a passage 206 through its length. An air vent 208 may also be provided on the one-piece dispensing apparatus 200.

A spike guard 146 may be provided to protect users from the sharp spike that may serve as the second activating member. Another optional feature of the dispensing apparatus 102 or 200 is an air inlet filter, not shown in the drawings. Such a filter may be useful to prevent particulates from blocking the air vent of the dispensing apparatus 102 and to maintain aseptic conditions. The filter may be separate from or combined with a hydrophobic membrane.

FIG. 10 illustrates an alternate cassette 300 having an outer surface with a recessed portion 302. A valve 304 is situated at the recessed portion of the cassette, reducing the likelihood that the valve or the valve connection to a container will be bumped or damaged during handling. The valve at the transfer port can be located in many different locations on the housing of the cassette in addition to the positions illustrated in FIG. 1 and in FIG. 10. For example, the valve may be located near the pressure plate 106. Alternatively, the valve could be recessed into the cassette housing in many ways. Any valve location that permits fluid communication with the inner reservoir 108 is within the scope of the present invention.

In one method of the present invention, the cassette 100 is provided to the patient filled with a liquid such as a diluent liquid. The flexible conduit 120 is closed using a clamp 160, for example, that pinches the flexible conduit 120. The patient may then remove the cap 144 from the valve 124 on the cassette. The dispensing apparatus 102 or 200 is coupled to the second portion 128 of the valve 124. The spike guard 146 is removed from the spike 134. The second activating member 132 or 204 is then used to pierce the septum 158, allowing a passage to be open to the cassette.

Figures 3, 4:
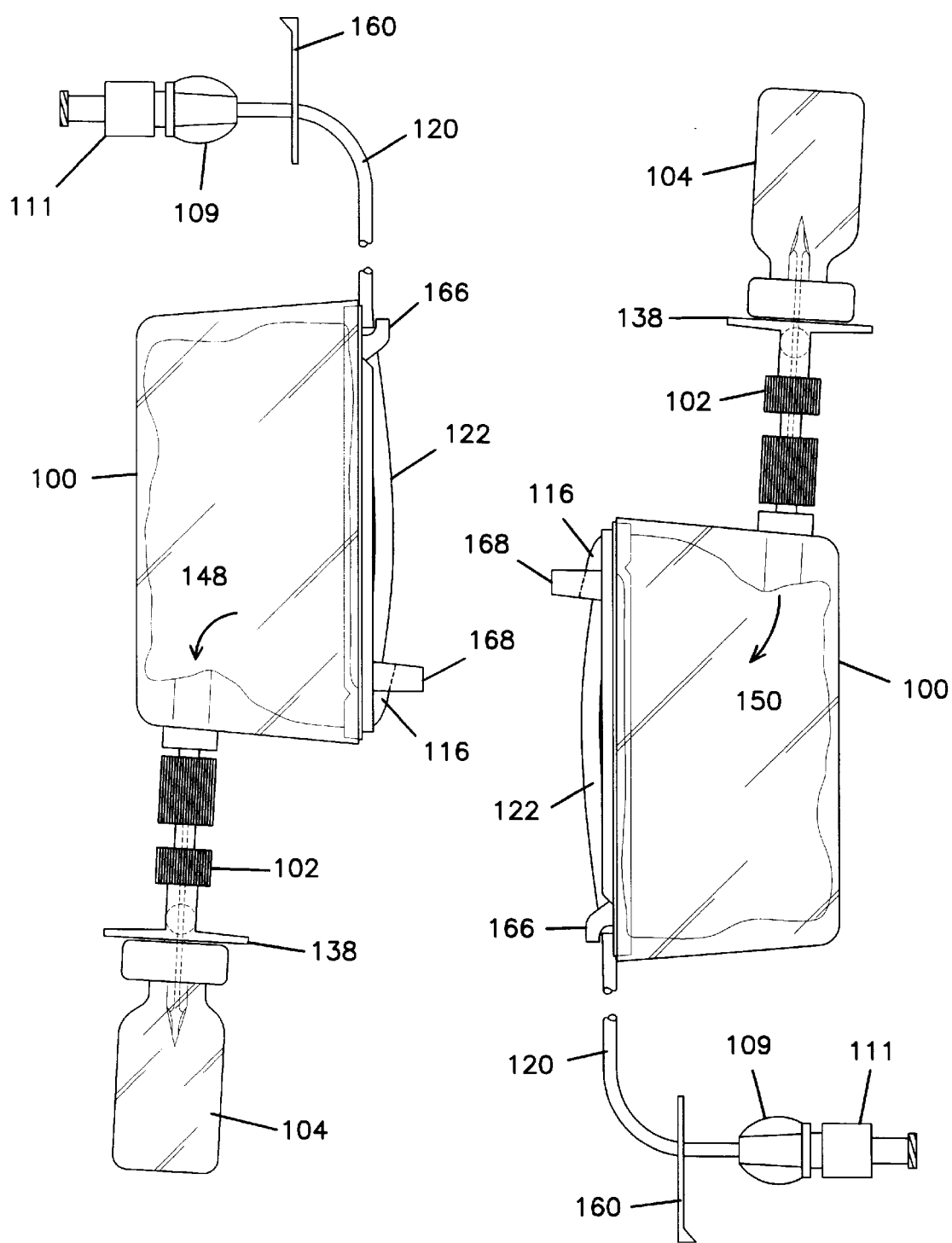
FIG. 3 is a side view of the connected cassette of FIG. 2, positioned so that liquid within the cassette flows into the medicant container.
FIG. 4 is a side view of the connected cassette of FIG. 2 positioned so that the drug in the medicant container flows back into the inner fluid reservoir of the cassette.

After the cassette 100, the dispensing apparatus 102 or 200, and the medicant container 104 are connected in fluid communication, the system is positioned with the cassette 100 on top, so that at least some of the liquid within the cassette 100 will flow into the medicant container 104, as shown in FIG. 3. by arrow 148. The liquid is thereby mixed with the powdered drug within the medicant container. The positioning of the system is then reversed so the medicant container 104 is on top, causing the mixed liquid drug within the medicant container 104 to flow through the dispensing apparatus 102 or 200 into the cassette 100 as indicated by arrow 150 in FIG. 4. The system may be tipped back and forth, as desired, to ensure complete mixing. Using this method, a user may easily and quickly reconstitute a powdered drug with a liquid at a location remote from a caregiver's office.

The present invention has been described thus far by way of example where the powdered drug is initially stored in the medicant container 104, and a liquid initially is stored in the cassette 100. However, as shown in FIG. 9, it is also possible to provide a cassette 180 initially containing the powdered drug. The cassette 180 is constructed in a similar manner as the cassette 100, noted above. In this case, a medicant container 182 would contain a liquid, as shown in FIG. 9. The powdered drug would be mixed by connecting a dispensing apparatus 186 with the valve 124 and the medicant container 182 in a similar manner as noted above. The system would first be positioned with the container 182 on top, allowing the liquid to flow into the inner reservoir 183 as indicated by the arrow 184. A mechanism for allowing the fluid to flow into the cassette is desirable with this type of arrangement. For example, an air vent may be provided on the connection between the medicant container and the cassette. A syringe could also be attached to the delivery tube to draw fluid from the medicant container into the cassette. A flexible medicant container could be used that could be squeezed to force fluid into the cassette. The dispensing apparatus 186 may then be disconnected from the cassette 180, and the cassette may be shaken to mix the powdered drug with the liquid.

Figure 12:
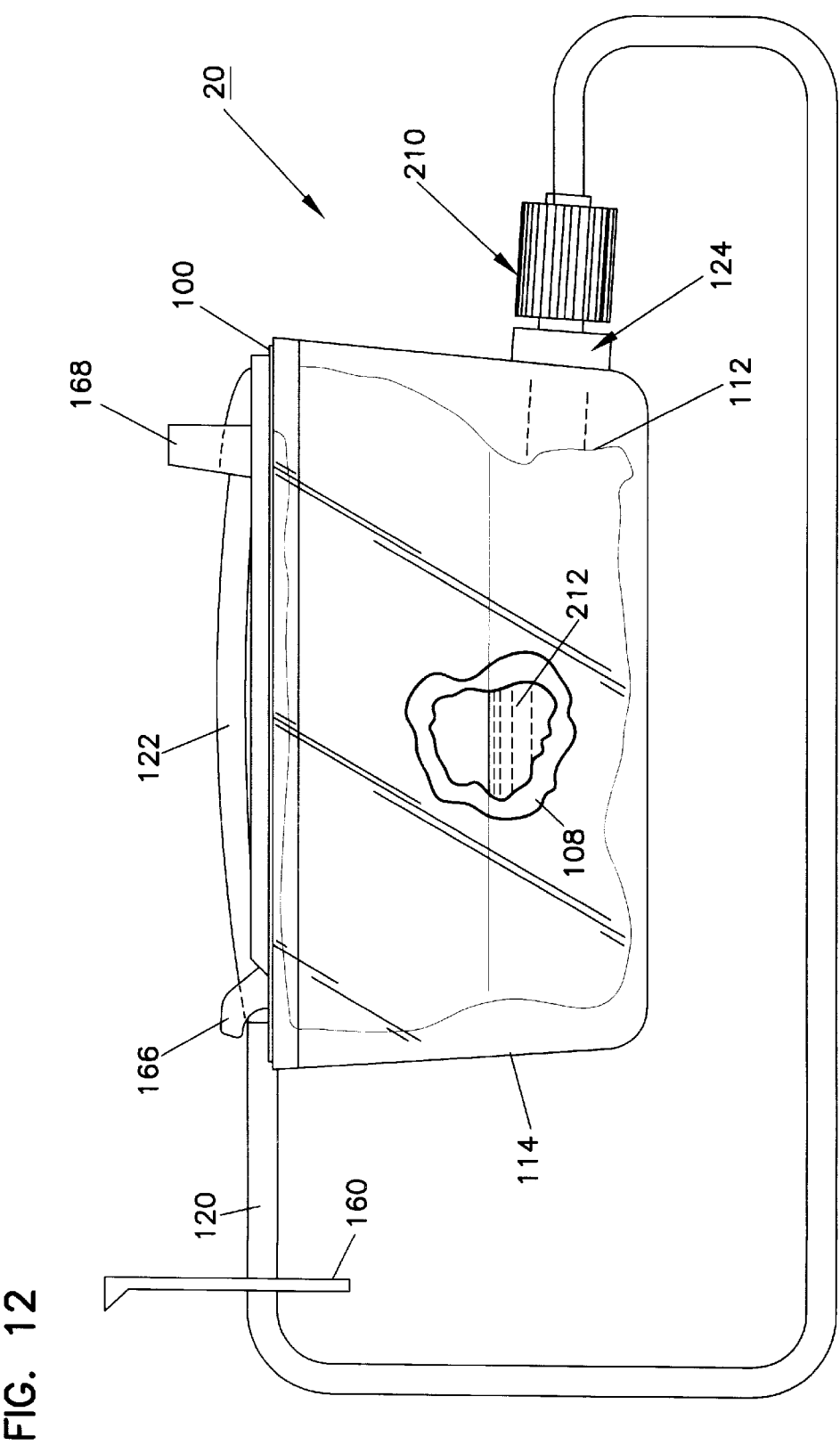
FIG. 12 is a side view of the cassette of the present invention during a mixing step.

The pumping mechanism 172 may be utilized in the method of the present invention to ensure that the reconstituted drug is thoroughly mixed, as illustrated in FIG. 12. The delivery conduit 120 may be connected using a luer fitting 210 to the valve 124. If the delivery conduit 120 is then acted upon by the pumping pads 172, the reconstituted drug 212 will be circulated within a closed system defined by the delivery conduit 120 and the inner reservoir 108. The control module 164 may be programmed to perform this mixing function for a predetermined amount of time. The amount of time for which mixing is performed in this manner may depend on the type of drug that is being reconstituted and its ability to dissolve within the diluent.

In another method of the present invention, the cassette 100 is filled with a liquid drug for administration to a patient and the transfer port 118 is utilized during the filling process to prevent air from being trapped in the inner reservoir 108 or delivery conduit 120. One source of trapped air is residual air that is in the inner reservoir 108 before it is filled. In the method of the present invention, this trapped air may be removed by attaching a syringe or other vacuum source to a second opening in the cassette, such as the transfer port. According to the invention, a small amount, or a first amount, of the drug is introduced into the cassette 100. The first amount of drug may be introduced to the inner reservoir of the cassette through the delivery conduit. Enough drug is introduced so that the delivery conduit is full, pushing all air that previously was in the delivery conduit into the inner reservoir.

Figure 13:
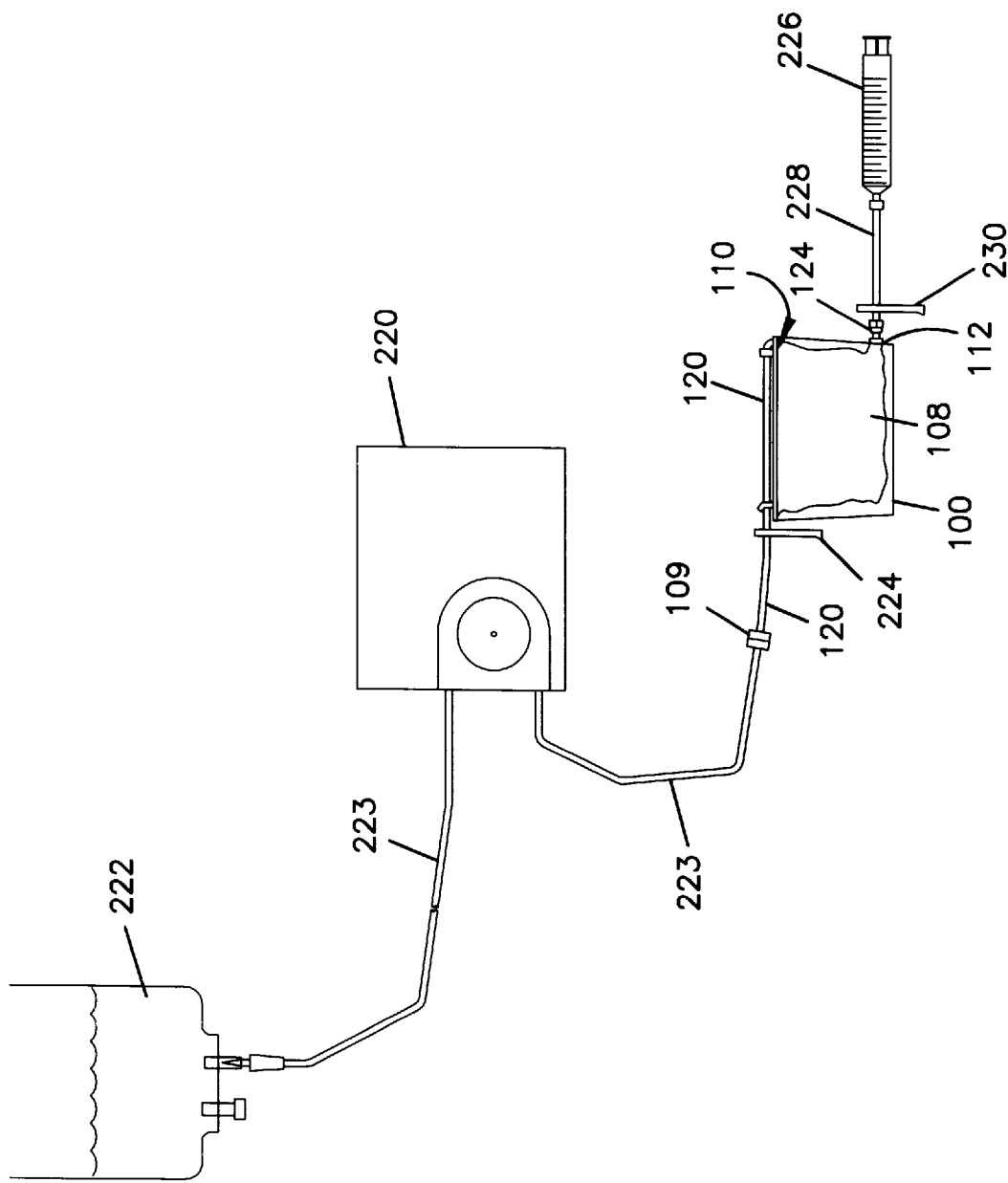
FIG. 13 is a plan view of a cassette filling system of the present invention for minimizing trapped air in the cassette.

The introduction of the first amount of drug into the cassette can take place in many different ways. For example, as illustrated in FIG. 13 a pharmacist may have a bulk dispensing pump 220 that is designed to pump the drug from, for example, a bulk supply reservoir container 222, into the delivery conduit 120. A conduit 223 may be coupled to an opening on the bulk reservoir 222, pass through the dispensing pump 220, and then connect to the connector 109 on the delivery conduit 120. The bulk dispensing pump 220 acts with a pumping action that is the reverse of the pumping action used when delivering drug from the inner reservoir to a patient. Further, many devices other than a bulk dispensing pump may be used to introduce the first amount of drug to the cassette, including a syringe, a pressurized supply or another pumping mechanism.

Once the delivery conduit 120 is filled with the first amount of drug, the delivery conduit 120 is clamped between the cassette and the drug supply using clamp 224. At this point, the delivery conduit 120 between the drug supply and the clamp 224 is filled with the drug and contains minimal, if any, trapped air. Then, a syringe 226 or vacuum source attached to the transfer port may be activated. The syringe 226 or vacuum source may alternately be attached before the introduction of the drug into the delivery conduit 120, if the tube 228 leading to the syringe 226 is clamped during introduction of the first amount, using a clamp 230. After the syringe or other vacuum source has evacuated the inner reservoir 108 through the transfer port 112, or second access port, the inner reservoir 108 and delivery conduit 120 up to the clamp 224 will be mostly devoid of gas and the first amount of drug. The valve at the transfer port 112 is then closed, or the clamp 230 is placed on the tube that leads away from the transfer port 112.

Next, a second amount of the drug is introduced into the cassette through the first access port 110. Preferably, the second amount of the drug is introduced into the inner reservoir 108 of the cassette 100 via the delivery conduit 120. The second amount of drug enters the evacuated inner reservoir 108 and air is therefore not trapped inside the inner reservoir 108. Preferably, the second amount of drug fills the inner reservoir 108 with the amount of drug necessary for providing the cassette to the patient.

The system and method for filling and minimizing entrapped air has thus far been described for use with a cassette 100 where a delivery conduit 120 is attached to the drug supply and the valve 124 at the transfer port 118 is attached to a syringe or vacuum source. However, it is also possible to utilize the method of the present invention where the vacuum source is attached to the delivery conduit 120 and a drug supply is attached to the valve 124 at the transfer port 118. The steps discussed above would similarly be carried out in this scenario. One consideration when utilizing this embodiment is that most luer-activated valves, and other types of valves, open when a spring-loaded plunger is depressed. It is possible, therefore, that the luer-activated valve may be opened by the pressure differential caused when the vacuum source is attached to the delivery conduit of the cassette. In this scenario, the luer-activated valve, or other valve used at the transfer port, will be configured to require more force to open the valve than is applied by the vacuum source.

A tamper-resistant cap, such as cap 144, may be supplied for the valve. The cap may be placed on the transfer port by a pharmacist or care provider after filling the cassette in order to offer additional security for the cassette. Tamper-resistant caps and other security features are especially important in the area of pain control. Many locking mechanisms to secure the cap 144 are well-known in the art, and may be used with the present invention.

The various embodiments described above are provided by way of illustration only and should not be construed to limit the invention. Those skilled in the art will readily recognize various modifications and changes which may be made to the present invention without strictly following the exemplary embodiments and applications illustrated and described herein, and without departing from the true spirit and scope of the present invention which is set forth in the following claims.

What is claimed is:

1. A method of mixing a drug for administration in a cassette, comprising:

providing a cassette including an outer housing, an inner reservoir structure within the outer housing, and a delivery conduit connectable to a patient, wherein the inner reservoir contains a liquid;

establishing fluid communication through a fluid transfer connection separate from the delivery conduit between the reservoir of the cassette and a medicant container containing a drug;

dispensing at least a portion of the liquid from the cassette into the medicant container to reconstitute the drug;

transferring the reconstituted drug into the reservoir; and disconnecting the fluid transfer connection between the reservoir of the cassette and the medicant container.

2. The method of claim 1, further comprising the step of providing a dispensing apparatus, and the step of establishing fluid communication further comprising establishing fluid communication between the dispensing apparatus and the cassette, and between the dispensing apparatus and the medicant container.

3. The method of claim 1, wherein the dispensing step includes positioning the cassette above the medicant container.

4. The method of claim 1, wherein the transferring step includes positioning the medicant container above the cassette.

5. A method of mixing a drug for administration in a cassette, comprising of:

providing a cassette including an outer housing, an inner reservoir structure within the outer housing, and a delivery conduit connectable to a patient, wherein the inner reservoir contains a powdered drug;

establishing fluid communication through a connection separate from the delivery conduit between the inner reservoir of the cassette and a medicant container containing a liquid;

dispensing the liquid from the medicant container to be mixed with the drug; and disconnecting the fluid transfer connection between the inner reservoir of the cassette and the medicant container.

6. A method of filling a cassette with a drug for administration using a drug pump, comprising:

providing a cassette including an inner reservoir structure in fluid communication with a first and second access port;

evacuating the inner reservoir through the second access port;

closing the second access port; and introducing the drug into the inner reservoir through the first access port.

7. The method of claim 6, further comprising the step of introducing an initial amount of the drug into the cassette before evacuating the inner reservoir.

8. The method of claim 6, wherein the cassette further includes a delivery conduit coupled to the first access port, and the step of introducing an initial amount of drug into the cassette comprises introducing the initial amount of drug into the delivery conduit.

9. The method of claim 8, further comprising the step of closing the delivery conduit before evacuating the inner reservoir.

10. The method of claim 6, further comprising the step of closing the second access port before introducing the drug through the first access port.

11. The method of claim 6, wherein the cassette further includes a delivery conduit coupled to the second access port, the step of evacuating the inner reservoir comprising evacuating the inner reservoir through the delivery conduit.

12. The method of claim 6, wherein the step of introducing comprises pumping the drug into the inner reservoir.

13. The method of claim 6, wherein introducing the drug comprises filling the inner reservoir.

14. A method of mixing a drug for administration in a cassette, comprising:

providing a cassette including an outer housing, an inner reservoir containing a liquid, and a delivery conduit connectable to a patient;

establishing fluid communication through a fluid transfer connection separate from the delivery conduit between the reservoir of the cassette and a medicant container containing a drug;

dispensing at least a portion of the liquid from the cassette into the medicant container to reconstitute the drug;

transferring the reconstituted drug into the cassette;

connecting the delivery conduit to the fluid transfer connection so the inner reservoir and delivery conduit define a closed system; and activating a pump mechanism on a portion of the delivery conduit to circulate the reconstituted drug within the closed system of the inner reservoir, whereby the reconstituted drug is further mixed.

* * * * *